US010930872B2

(12) United States Patent
Yonekawa et al.

(10) Patent No.: US 10,930,872 B2
(45) Date of Patent: Feb. 23, 2021

(54) LIGHT-EMITTING ELECTROCHEMICAL CELL, COMPOSITION FOR FORMING LIGHT-EMITTING LAYER OF LIGHT-EMITTING ELECTROCHEMICAL CELL, AND IONIC COMPOUND FOR LIGHT-EMITTING LAYER OF LIGHT-EMITTING ELECTROCHEMICAL CELL

(71) Applicant: Nippon Chemical Industrial Co., Ltd., Tokyo (JP)

(72) Inventors: Fumihiro Yonekawa, Tokyo (JP); Yohei Mizuguchi, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 302 days.

(21) Appl. No.: 15/767,927

(22) PCT Filed: Nov. 8, 2016

(86) PCT No.: PCT/JP2016/083129
§ 371 (c)(1),
(2) Date: Apr. 12, 2018

(87) PCT Pub. No.: WO2017/094458
PCT Pub. Date: Jun. 8, 2017

(65) Prior Publication Data
US 2018/0301653 A1     Oct. 18, 2018

(30) Foreign Application Priority Data
Nov. 30, 2015  (JP) .............................. JP2015-233909

(51) Int. Cl.
*H01L 51/00* (2006.01)
*H01L 51/50* (2006.01)
(Continued)

(52) U.S. Cl.
CPC ........ *H01L 51/5032* (2013.01); *C07C 309/30* (2013.01); *C07C 309/31* (2013.01);
(Continued)

(58) Field of Classification Search
CPC .................................................. H01L 51/5032
See application file for complete search history.

(56) References Cited

U.S. PATENT DOCUMENTS 5,682,043 A * 10/1997 Pei ........................... F21K 2/08
257/102
7,679,082 B2    3/2010 Ling et al.
(Continued)

FOREIGN PATENT DOCUMENTS

| CN | 101128506 A | 2/2008 |
|---|---|---|
| CN | 106796001 A | 5/2017 |

(Continued)

OTHER PUBLICATIONS

Kohno et al., Aust. J. Chem. 2011, 64, 1560-1567.*
(Continued)

*Primary Examiner* — Vu A Nguyen
(74) *Attorney, Agent, or Firm* — Westerman, Hattori, Daniels & Adrian, LLP

(57) ABSTRACT

A light-emitting electrochemical cell has a light-emitting layer and electrodes and disposed on the respective surface thereof. The light-emitting layer includes an organic polymeric light-emitting material and an ionic compound represented by the general formula (1). The ring $A^1$ denotes an aromatic ring; X is S, C or P; $R^1$ denotes R' or OR', and R' denotes an alkyl group; n denotes 0 or 1; B denotes O, $OR^2$ or $A^2$, $R^2$ denotes a saturated hydrocarbon group, and $A^2$ denotes an aromatic ring; the bond a is a single bond or a double bond; the bond a between B and X is a double bond
(Continued)

and B is O; when X is P, the bond a between B and X is a single bond and B is $OR^2$ or $A^2$; d is 1 or more; and $Y^+$ denotes a cation.

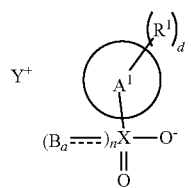

(1)

6 Claims, 7 Drawing Sheets

(51) Int. Cl.
 C09K 11/06 (2006.01)
 C09K 11/08 (2006.01)
 C07F 9/54 (2006.01)
 H05B 33/14 (2006.01)
 H05B 33/20 (2006.01)
 C07C 309/31 (2006.01)
 C07C 309/30 (2006.01)
 F21K 2/08 (2006.01)
 C09K 11/02 (2006.01)

(52) U.S. Cl.
 CPC .............. *C07F 9/54* (2013.01); *C09K 11/025* (2013.01); *C09K 11/06* (2013.01); *F21K 2/08* (2013.01); *H01L 51/0058* (2013.01); *H01L 51/0067* (2013.01); *H01L 51/0085* (2013.01); *H01L 51/50* (2013.01); *H05B 33/14* (2013.01); *H05B 33/20* (2013.01)

(56) References Cited

U.S. PATENT DOCUMENTS

| 2007/0290199 A1 | 12/2007 | Ling et al. |
| 2014/0014885 A1 | 1/2014 | Pan et al. |
| 2014/0249606 A1 | 9/2014 | Pan et al. |
| 2017/0294616 A1 | 10/2017 | Yonekawa |

FOREIGN PATENT DOCUMENTS

| EP | 2 447 334 A2 | 5/2012 |
| EP | 2 952 518 A1 | 12/2015 |
| EP | 3 205 924 A1 | 8/2017 |
| JP | 2004-59831 A | 2/2004 |
| JP | 2011-103234 A | 5/2011 |
| JP | 2013-30527 A | 2/2013 |
| JP | 2013-171968 A | 9/2013 |
| JP | 2014-511832 A | 5/2014 |
| JP | 2014-519190 A | 8/2014 |
| WO | 2006/052222 A2 | 5/2006 |
| WO | 2010/085180 A1 | 7/2010 |
| WO | 2012/126566 A1 | 9/2012 |

OTHER PUBLICATIONS

Shin et al., "Light-Emitting Electrochemical Cells with Millimeter-Sized Interelectrode Gap: Low-Voltage Operation at Room Temperature", J. Am. Chem. Soc., 2006, vol. 128, pp. 15568-15569, cited in Specification (2 pages).
Pei et al., "Polymer Light—Emitting Electrochemical Cells", Science, Aug. 25, 1995, vol. 269, pp. 1086-1088, cited in ISR (4 pages).
International Search Report dated Jan. 24, 2017, issued in counterpart International Application No. PCT/JP2016/083129 (2 pages).
Extended (Supplementary) European Search Report dated Oct. 17, 2018, issued in counterpart application No. 16870398.1. (9 pages).

\* cited by examiner

[Figure 1]
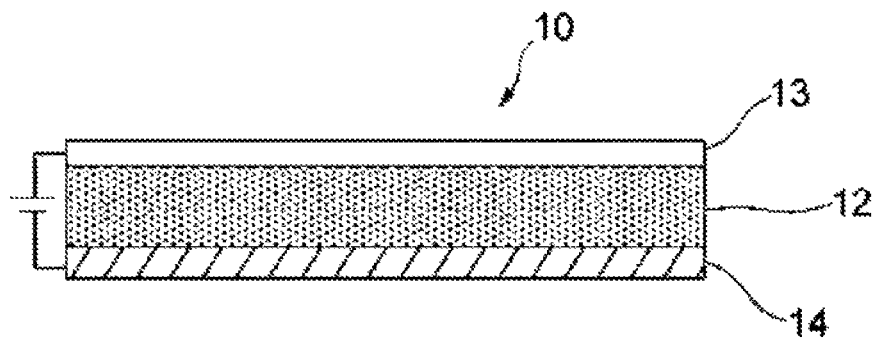
[Figure 2 (a)]                [Figure 2 (b)]
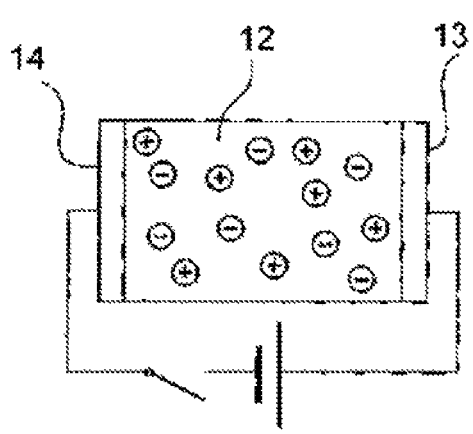 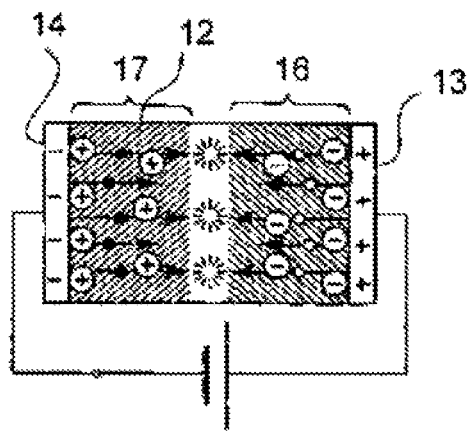

[Figure 3]
Example 2-4
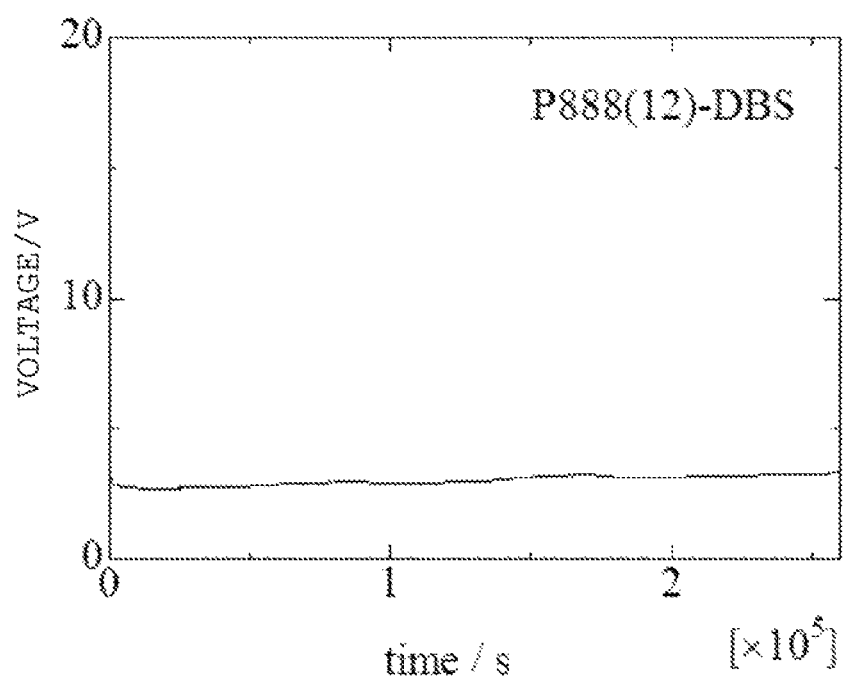

[Figure 4]
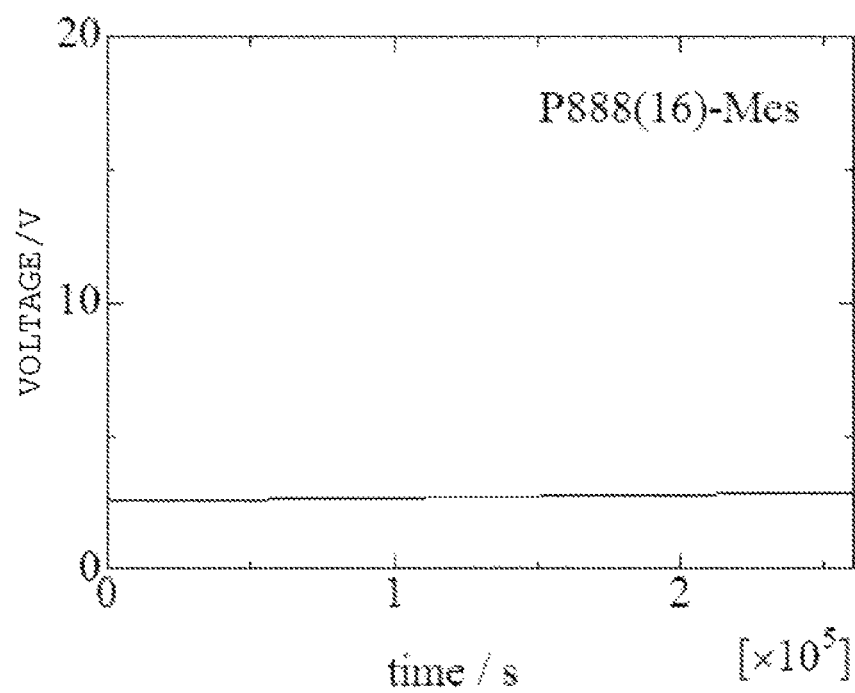

[Figure 5]
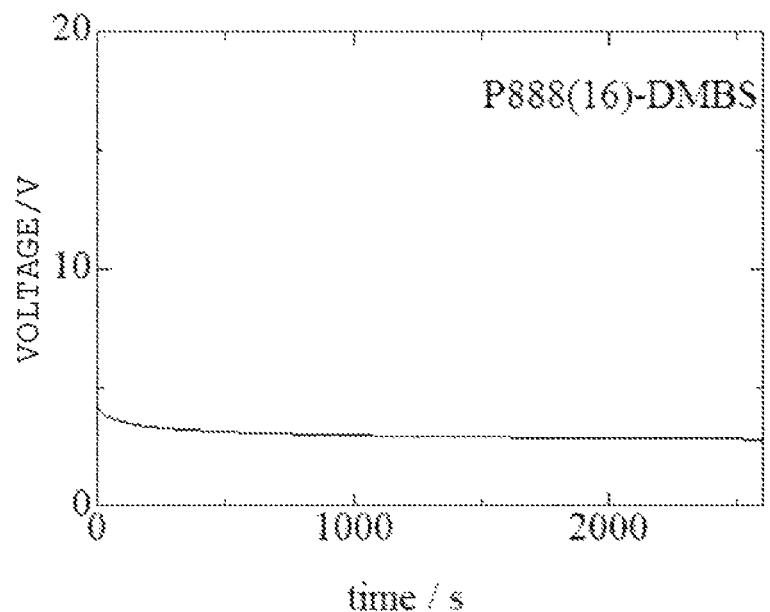

[Figure 6]
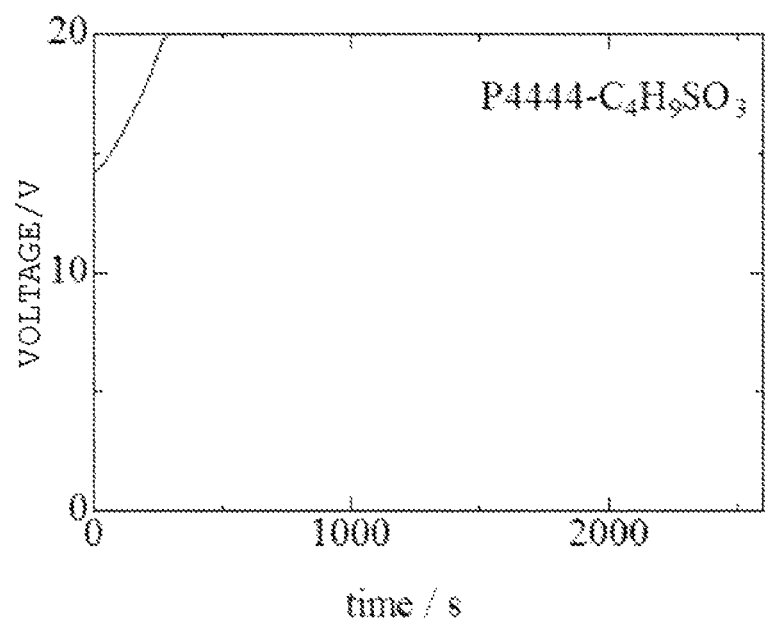

[Figure 7]
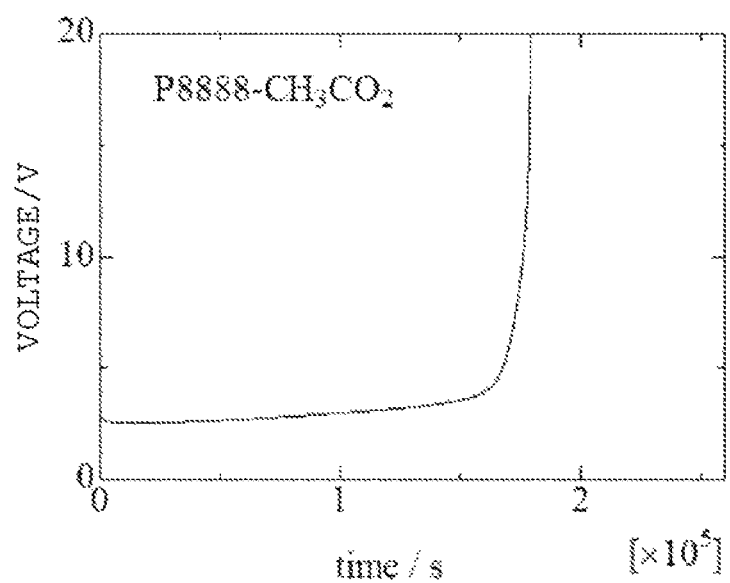

[Figure 8]
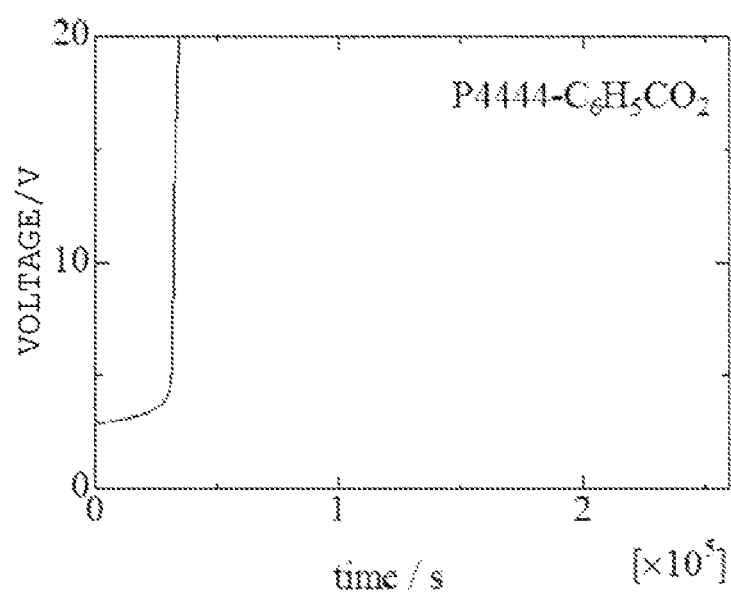
Comparative Example 2-6

LIGHT-EMITTING ELECTROCHEMICAL CELL, COMPOSITION FOR FORMING LIGHT-EMITTING LAYER OF LIGHT-EMITTING ELECTROCHEMICAL CELL, AND IONIC COMPOUND FOR LIGHT-EMITTING LAYER OF LIGHT-EMITTING ELECTROCHEMICAL CELL

TECHNICAL FIELD

The present invention relates to a light-emitting electrochemical cell having a light-emitting layer comprising a light-emitting material and an ionic compound. Further the present invention relates to a composition for forming a light-emitting layer of a light-emitting electrochemical cell, and an ionic compound for a light-emitting layer thereof.

BACKGROUND ART

In recent years, there are drastically progressing developments of organic electroluminescent (organic EL) devices which are self-luminous devices with electrons and holes as carriers. Organic EL has features of being capable of achieving more thickness reduction and weight reduction and being better in visibility than liquid crystal devices, which necessitate backlights and are non-self-luminous.

The organic EL devices usually have a pair of substrates on surfaces facing each other of which respective electrodes are formed, and a light-emitting layer disposed between the pair of substrates. Among these, the light-emitting layer is composed of an organic thin film containing a light-emitting material to emit light by application of a voltage. When such organic EL devices are made to emit light, holes and electrons are injected by applying a voltage from an anode and a cathode to the organic thin film. Thereby, light emission can be obtained doe to that holes and electrons are caused to be recombined in the organic thin film and excitons produced by the recombination return to their ground state.

In the organic EL devices, in addition to the light-emitting layer, a hole injection layer and an electron injection layer to raise the injection efficiency of holes and electrons, and a hole transport layer and an electron transport layer to improve the recombination efficiency of holes and electrons, respectively, must be provided between the light-emitting layer and the electrodes. Hence, the organic EL devices come to have a multilayer structure, making the structure complex and increasing the number of the production processes. Further the organic EL devices have many restrictions, since the work functions must be taken into consideration in selection of electrode materials to be used for anodes and cathodes.

As self-luminous devices coping with these problems, light-emitting electrochemical cells (LECs) have recently attracted attention. The light-emitting electrochemical cells generally have a light-emitting layer containing a salt and an organic light-emitting material. In the voltage application, cations and anions originated from the salt migrate in the light-emitting layer toward a cathode and an anode, respectively, and make large electric field gradients (electric double layers) at electrode interfaces. Since the formed electric double layers facilitate injection of electrons and holes at the cathode and anode, respectively, the light-emitting electrochemical cells have no need of having a multilayer structure as in organic EL. Further since the work functions of materials to be used as cathodes and anodes are not required to be taken into consideration for the light-emitting electrochemical cells, there are few restrictions on the materials. For these reasons, the light-emitting electrochemical cells are expected as self-luminous devices capable of reducing the production cost more largely as compared with the organic EL.

As salts to be used for light-emitting electrochemical cells, lithium salts, potassium salts and the like are often used among inorganic salts; and ionic compounds such as ion liquids are often used among organic salts (for example, see Patent Literatures 1 to 4). Merits of using these salts and ionic compounds include that electric double layers tend to be easily formed due to easy re-orientation at electrode interfaces, and injection of holes and electrons becomes easy.

Particularly when an organic ionic compound such as an ion liquid is used as described in Patent Literature 1 and Patent Literature 2, the re-orientation velocity at electrode interfaces can be increased. Hence, studies on light-emitting layers using organic ionic compounds are being carried out. Further Patent Literature 5 states that the use of a non-polymeric organic ionic compound containing one ion having a functional organic group and another ion which is so small as to function as mobile ions in a film containing the organic ionic compound improves the life and the efficiency of organic light-emitting electrochemical devices such as OLECs ("organic light-emitting electrochemical cells", so-called LECs). The Patent Literature states that the non-polymeric organic ionic compound is composed of a mono-charged organic cationic compound and a mono-charged anionic compound. Non Patent Literature 1 proposes, as an ionic compound to be used for a light-emitting electrochemical cell, a compound composed of an imidazolium-based cation and a sulfate ester-based anion.

CITATION LIST

Patent Literature

Patent Literature 1: Japanese Patent Laid-Open No. 2011-103234

Patent Literature 2: International Publication No. WO 2010/085130

Patent Literature 3: Japanese Patent Laid-Open No. 2013-171968

Patent Literature 4: European Patent No. 2447334

Patent Literature 5: International Publication No. WO 2012/126566

Non Patent Literature

Non Patent Literature 1: J. Chem. Soc., vol. 128, p. 15568-15569 (2006)

SUMMARY OF INVENTION

The present invention provides a light-emitting electrochemical cell having a light-emitting layer and an electrode disposed on each surface thereof, wherein the light-emitting layer comprises a light-emitting material and an ionic compound; and the ionic compound is represented by the following general formula (1).

[Formula 1]

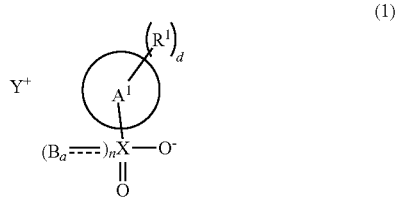

(1)

wherein the ring $A^1$ denotes an aromatic ring; X denotes a sulfur atom, a carbon atom or a phosphorus atom; $R^1$ denotes R' or OR', and R' denotes an alkyl group; n denotes 0 or 1; B denotes an oxygen atom, $OR^2$ or $A^2$, $R^2$ denotes a saturated hydrocarbon group, and $A^2$ denotes an aromatic ring which may be identical with or different from the ring $A^1$ in the formula; the bond a is a single bond or a double bond; when X is a carbon atom, n is 0; when X is a sulfur atom, n is 0 or 1, and when n is 1, the bond a between B and X is a double bond and B is an oxygen atom; when X is a phosphorus atom, n is 1, and in this case, the bond a between B and X is a single bond and B is $OR^2$ or $A^2$; d is 1 or more and is the number of substitutable positions in the ring $A^1$, and when d is 2 or more, a plurality of $R^1$ present may be identical or different; and $Y^+$ denotes a cation.

The present invention, further provides a composition for forming a light-emitting layer of a light-emitting electrochemical cell, the composition comprising an ionic compound represented by the above general formula (1), a light-emitting material, and a solvent.

The present invention further provides an ionic compound for a light-emitting layer of a light-emitting electrochemical cell, the ionic compound comprising a compound represented by the above general formula (1).

BRIEF DESCRIPTION OF DRAWINGS

FIG. 1 is a schematic cross-sectional view of a light-emitting electrochemical cell in one embodiment of the present invention.

FIGS. 2(a) and 2(b) are a conceptual view illustrating a light emission mechanism of a light-emitting electrochemical cell; and FIG. 2(a) illustrates the light-emitting electrochemical cell before a voltage application, and FIG. 2(b) illustrates the light-emitting electrochemical cell after the voltage application.

FIG. 3 shows a measurement result of an over-time change in the voltage of a light-emitting electrochemical cell in Example 2-4.

FIG. 4 shows a measurement result of an over-time change in the voltage of a light-emitting electrochemical cell in Example 2-7.

FIG. 5 shows a measurement result of an over-time change in the voltage of a light-emitting electrochemical cell in Example 2-8.

FIG. 6 shows a measurement result of an over-time change in the voltage of a light-emitting electrochemical cell in Comparative Example 2-2.

FIG. 7 shows a measurement result of an over-time change in the voltage of a light-emitting electrochemical cell in Comparative Example 2-4.

FIG. 8 shows a measurement result of an over-time change in the voltage of a light-emitting electrochemical cell in Comparative Example 2-6.

DETAILED DESCRIPTION OF INVENTION

Conventional light-emitting electrochemical cells using an organic ionic compound have such a problem that the emission luminance at low voltages is low and the luminous efficiency is low. The cells further have also such a problem that the voltage value required for providing a certain luminance rises over time.

As a result of exhaustive studied in order to solve the above problems, the present inventors have found that a light-emitting electrochemical cell using an ionic compound having a specific anion can astonishingly provide a high luminance at a low voltage, and has a high emission efficiency and a high over-time stability of the voltage required for providing a certain luminance. The present inventors have thereby completed the present invention.

Hereinafter, a preferred embodiment of the light-emitting electrochemical cell of the present invention will be described by reference to the drawings. As described later, a light-emitting electrochemical cell 10 of the present embodiment has one feature in that as an anion of an ionic compound, a specific one is used.

As shown in FIG. 1, the light-emitting electrochemical cell 10 of the present embodiment has a light-emitting layer 12 and electrodes 13, 14 disposed on the respective surfaces thereof. The light-emitting electrochemical cell 10 has the first electrode 13 and the second electrode 14 being a pair of electrodes facing each other, and the light-emitting layer 12 interposed between the pair of electrodes 13, 14. The light-emitting electrochemical cell 10 is so configured that the light-emitting layer emits light by application of a voltage. The light-emitting electrochemical cell 10 is one to be used as various types of displays and the like. FIG. 1 illustrates such a state that a direct current power source is used as a power source; and the first electrode 13 is connected to a positive pole of the direct current power source, and the second electrode 14 is connected to a negative pole thereof. However, contrary to the illustration, the first electrode 13 may be connected to the negative pole, and the second electrode 14 may be connected to the positive pole. Further, in place of the direct current power source as the power source, an alternating current power source may also be used.

The first electrode 13 and the second electrode 14 may be transparent electrodes having light transmissivity, or may be translucent or opaque electrodes. The transparent electrodes having light transmissivity include those composed of a metal oxide such as an indium-doped tin oxide (ITO) or a fluorine-doped tin oxide (FTO), and further include those composed of a polymer having transparency, such as an impurity-added poly(3,4-ethylenedioxythiophene) (PEDOT). Examples of the translucent or opaque electrodes include metallic materials such as aluminum (Al), silver (Ag), gold (Au), Platinum (Pt), tin (Sn), bismuth (Bi), copper (Cu), chromium (Cr), zinc (Zn) and magnesium (Mg).

It is preferable that at least one of the first electrode 13 and the second electrode 14 is made as a transparent electrode, because light emitted from the light-emitting layer 12 can easily be extracted outside. Further it is preferable that one thereof be made as a transparent electrode and the other thereof is made as an opaque metal electrode, because light emitted from the light-emitting layer 12 can be extracted outside while being reflected from the metal electrode. Further both of the first electrode 13 and the second electrode 14 may also be made as transparent electrodes to make a see-through emitter. Further by making both of the first electrode 13 and the second electrode 14 as metal electrodes composed of Ag or the like, which is a material having a high reflectance, and by regulating the film thickness of the light-emitting layer 12, the light-emitting electrochemical cell 10 can also be made to be a laser oscillating device.

When the first electrode 13 is made as a transparent electrode and the second electrode 14 is made as an opaque or translucent metal electrode, the first electrode 13 preferably has a thickness of, for example, 10 nm or larger and 500 nm or smaller from the viewpoint of realizing a suitable resistivity and light transmissivity. The second electrode 14 preferably has a thickness of, for example, 10 nm or larger and 500 nm or smaller from, the viewpoint of realizing a suitable resistivity and light transmissivity as in the first electrode 13.

The light-emitting layer 12 is made by mixing a light-emitting material and an ionic compound. The light-emitting layer 12 may be in either of a solid state and a liquid state. When the light-emitting layer 12 is in a solid state, the light-emitting layer 12 can maintain its definite shape and resist to a force applied from outside.

In the present invention, the light-emitting material refers to one which functions as carriers of electrons and holes (having transport functions of holes and electrons) by being doped with an anion and a cation, and excites and emits light (having a light-emitting function) by combination of electrons and holes. Therefore, in the present invention, the expression called simply "light-emitting material" means a conductive light-emitting material. In the present invention, the light-emitting material may be a material having both the transport functions of holes and electrons and the light-emitting function, or may be a combination of a material having the transport functions of holes and/or electrons with a material to receive holes and electrons from the former material and emit light.

In the former case, the material having both the transport functions of holes and electrons and the light-emitting function includes organic polymeric light-emitting materials described later. Then in the latter case, the material having the functions of transporting holes and/or electrons includes organic polymeric conductive materials. As described later, the organic polymeric conductive materials include, in addition to organic polymeric light-emitting materials, organic polymers, such as polyvinylcarbazole, having conductivity but no light-emitting function or a low light-emitting function. Then as the material having the functions to receive holes and electrons from the material transporting holes and/or electrons and emit light, materials other than organic polymers are usually used, and the materials include metal complexes, organic low-molecular materials and quantum dot materials described later. In the present description, also an organic polymeric conductive material having no light-emitting function or a low light-emitting function, in the case of being used as a combination with a light-emitting material other than an organic polymer such as a metal complex, an organic low-molecular material or a quantum dot material, is thus included in a "light-emitting material". For example, the "compatibility with the light-emitting material" described later, in the case of using, as a light-emitting material, a combination of the organic polymeric conductive material with the metal complex, organic low-molecular material or quantum dot material, includes the compatibility with the conductive material in the light-emitting material.

The ionic compound included in the light-emitting layer is a substance to make the mobility of ions to be secured, electric double layers to be easily formed and the injection of holes and electrons to be facilitated. In the present embodiment, as the ionic compound, one represented by the above general formula (1) is used.

The ionic compound represented by the general formula (1) (hereinafter, referred to also as "ionic compound (1)" has one feature in that a specific anion is used as its anion. The present inventors have studied on structures of ionic compounds capable of providing a light-emitting electrochemical cell high in luminous efficiency and high in voltage stability. As a result, it has been found that when an ionic compound having an anion having a structure in which an anionic group having a structure represented by "—(X=O)O⁻" (X is a sulfur atom, a carbon atom or a phosphorus atom) is bonded to an aromatic ring, and an alkyl group, or an alkoxy group is bonded to the aromatic ring is used for a light-emitting electrochemical cell, due to high compatibility with the light-emitting material, there can be provided a light-emitting electrochemical cell not only being capable of providing a high luminance at a low voltage and being high in the luminous efficiency, but also being low in the degree of over-time change in the voltage required for providing a certain luminance and being high in the reliability. The small over-time change in the voltage is indicated by the small rise in an applied voltage to make a certain current to flow, and sometimes called, for example, voltage withstandability. The above anionic group is specifically a sulfonate group, a sulfinate group, a phosphonate group, a phosphinate group or a carboxyl group.

In the general formula (1), the aromatic ring represented by the ring $A^1$ may or may not contain a heteroatom(s) as its constituting atoms. The aromatic ring containing no heteroatom includes a benzene ring, a naphthalene ring, an anthracene ring, a pyrene ring, a phenanthrene ring, a fluorene ring, a triphenylene ring, a naphthacene ring, a methylphenyl ring and a dimethylphenyl ring.

Further the aromatic ring containing a heteroatom(s) includes a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazan ring, a tetrazole ring, a pyran ring, a thiin ring, a pyridine ring, a piperidine ring, an oxazine ring, a morpholine ring, a thiazine ring, a pyridazine ring, a pyrimidine ring, a pyrazine ring, a piperazine ring, a triazine ring, a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a dibenzothiophene ring, a carbazole ring, a xanthene ring, an acridine ring, a phenanthridine ring, a phenanthroline ring, a phenazine ring, a phenoxazine ring, a thianthrene ring, an indolizine ring, a quinolizine ring, a quinuclidine ring, a naphthyridine ring, a purine ring and a pteridine ring.

In the general formula (1), Fr bonded to the ring $A^1$ is R' or OR', and R' denotes an alkyl group. The alkyl group represented by R' may be any of branched-chain, straight-chain and cyclic alkyl groups, but is preferably a branched-chain or straight-chain alkyl group. Examples of the branched-chain or straight-chain alkyl group include a methyl group, an ethyl group, a propyl group, an isopropyl group, an n-butyl group, an s-butyl group, a t-butyl group, an isobutyl group, an amyl group, an isoamyl group, a t-amyl group, a hexyl group, a heptyl group, an isoheptyl group, a t-heptyl group, an n-octyl group, an isooctyl group, a 2-ethylhexyl group, a t-octyl group, a nonyl group, an isononyl group, a decyl group, an isodecyl group, an undecyl group, a dodecyl group, a tridecyl group, an isotridecyl group, a tetradecyl group, a hexadecyl group, an octadecyl group and an icosyl group. The cyclic alkyl group includes a cyclopentyl group, a cyclohexyl group, a methylcyclohexyl group, a dimethylcyclohexyl group, a cycloheptyl group and a cyclooctyl group.

In the formula (1), when X is a phosphorus atom, B is $OR^2$ or $A^2$.

In the formula (1), when B is $OR^2$, the saturated hydrocarbon group represented by $R^2$ includes, in addition to various alkyl groups cited as examples of alkyl groups represented by the above R', polycyclic hydrocarbon groups. Examples of the polycyclic hydrocarbon groups include a decahydronaphthyl group, an adamntyl group, a norbornyl group and a methylnorbornyl group.

When B is $A^2$, the aromatic ring represented by the $A^2$ includes the same groups as the groups cited above as examples of the ring $A^1$. In the ring $A^2$, one or more hydrogen atoms are preferably replaced with $R^1$. The $R^1$ with which the ring $A^2$ is substituted in this case may be identical with or different from the $R^1$ with which the ring $A^1$ is substituted; then when the ring $A^2$ is substituted with a plurality of $R^1$, these $R^1$ may be identical or different. When the ring $A^2$ is substituted with a plurality of $R^1$, the upper limit of the number of substitutions is the number of substitutable positions on the ring $A^2$. Further a preferable upper limit of the number of substitutions can be quoted from the same upper limit as a preferable upper limit, described later, of the number of substitutions d with $R^1$ on the ring $A^1$.

One or more hydrogen atoms in the ring $A^1$ and the ring $A^2$ each may or may not be substituted with a substituent other than $R^1$; and examples of the substituent other than $R^1$, when substituted, includes an amino group, a nitrile group, a phenyl group and a benzyl group. For example, when hydrogen atoms in the ring $A^1$ and the ring $A^2$ are replaced with an aromatic ring-containing hydrocarbon group other than $R^1$, such as a phenyl group or a benzyl group, one or two or more hydrogen atoms on the aromatic ring in the aromatic ring-containing hydrocarbon group are preferably replaced with $R^1$. A preferable upper limit of the number of substitutions in this case can be quoted from the same upper limit as a preferable upper limit, described later, of the number of substitutions d with $R^1$ on the ring $A^1$. One or two or more hydrogen atoms in the above aromatic ring may be replaced with, in addition to $R^1$, an amino group, a nitrile group and a carboxyl group.

Here, when a hydrogen atom(s) of the ring $A^1$ and the ring $A^2$ each is replaced with a substituent other than $R^1$, the total of the number of the substituents other than $R^1$ and d on the ring $A^1$ and the ring $A^2$ each needs to be the number of substitutable positions or less on the ring $A^1$ and the ring $A^2$ each. For example, when the ring $A^1$ is a benzene ring, the number of substitutable positions on the ring $A^1$ is 5.

One or more hydrogen atoms in $R^1$ and $R^2$ each may or may not be replaced with a substituent; and examples of the substituent in the case of being substituted includes an amino group, a nitrile group, a phenyl group and a benzyl group. For example, when one or two or more hydrogen atoms in $R^1$ and $R^2$ each are replaced with an aromatic ring-containing hydrocarbon group such as a phenyl group or a benzyl group, one or two or more hydrogen atoms on the aromatic ring in the aromatic ring-containing hydrocarbon group are preferably replaced with $R^1$. Further, one or two or more hydrogen atoms in the above aromatic ring may be replaced with, in addition to $R^1$, an amino group, a nitrile group and a carboxyl group.

From the viewpoint of easy availability of the ionic compound (1) and enhancement of the compatibility of the ionic compound (1) with the light-emitting material, and from the viewpoint of the low-voltage drive, the number of carbon atoms of the alkyl group represented by R' is preferably 1 or larger and 12 or smaller, more preferably 2 or larger and 10 or smaller, and especially preferably 3 or larger and 8 or smaller.

From the viewpoint of enhancement of the compatibility of the ionic compound (1) with the light-emitting material, and from the viewpoint of the low-voltage drive, the ring $A^1$ of the ionic compound (1) is preferably a ring having the number of atoms constituting the ring of 3 or more and 12 or less, more preferably a ring having the number of 5 or more and 10 or less, and especially preferably a ring having the number of 6 or more and 8 or less. Rings preferable as the ring $A^1$ include a benzene ring.

The number of substitutions d with $R^1$ on the ring $A^1$ is the number of substitutable positions on the ring $A^1$, and is, though depending on the kind of the ring $A^1$, in consideration of the kind of the preferable ring $A^1$ and the easy availability of the ionic compound (1), preferably 9 or smaller, preferably 6 or smaller, and preferably 4 or smaller. Particularly when the ring $A^1$ is a benzene ring, d is preferably 4 or smaller, and especially preferably 3 or smaller. When the ring $A^1$ has a plurality of $R^1$, the total of the numbers of carbon atoms of the plurality of $R^1$ is preferably 3 or larger and 108 or smaller, and more preferably 6 or larger and 64 or smaller.

The bonding position of $R^1$ on the ring $A^1$ may be any position with respect to the bonding position of a sulfur atom, a carbon atom or a phosphorus atom represented by X. For example, when the ring $A^1$ is a benzene ring, the position may be any of the para position, the meta position and the ortho position. The para position is preferable from the viewpoint of the easy availability, and the ortho position is preferable from the viewpoint of the low-voltage drive.

When the anion of the ionic compound (1) has a plurality of $R^1$, the difference in the number of carbon atoms between these $R^1$ is preferably 0 or larger and 5 or smaller, and more preferably 0 or larger and 3 or smaller. Since use of an anion having such a structure enables the compatibility with the light-emitting material to be maintained and the excellent luminous property to be exhibited, it is preferable.

Examples of the anion, in which in the formula (1), X is a sulfur atom and n is 1 include dodecylbenzenesulfonate, mesitylenesulfonate, 4-t-butyl-2,6-dimethylbenzenesulfonate; toluenesulfonate, ethylbenzenesulfonate, propylbenzenesulfonate, butylbenzenesulfonate, octylbenzenesulfonate or laurylbenzenesulfonate, in which the position of the alkyl group with respect to the sulfonate group is any of the para, meta and ortho positions; 2,4-dimethylbenzenesulfonate, 2-naphthalenesulfonate, 1-alkyl-2-naphthalenesulfonates, 3-alkyl-2-naphthalenesulfonates, 4-alkyl-2-naphthalenesulfonates, 5-alkyl-2-naphthalenesulfonates, 6-alkyl-2-naphthalenesulfonates, 7-alkyl-2-naphthalenesulfonates and 8-alkyl-2-naphthalenesulfonates. Examples of the anion in which X in the formula (1) is a sulfur atom and n is 0 include dodecylbenzenesulfinate, mesitylenesulfinate, 4-t-butyl-2,6-dimethylbenzenesulfinate; toluenesulfinate, ethylbenzenesulfinate, propylbenzenesulfinate, butylbenzenesulfinate, octylbenzenesulfinate or laurylbenzenesulfinate, in which the position of the alkyl group with respect to the sulfinate group is any of the para, meta and ortho positions; 2,4-dimethylbenzenesulfinate, 2-naphthalenesulfinate, 1-alkyl-2-naphthalenesulfinates, 3-alkyl-2-naphthalenesulfinates, 4-alkyl-2-naphthalenesulfinates, 5-alkyl-2-naphthalenesulfinates, 6-alkyl-2-naphthalenesulfinates, 7-alkyl-2-naphthalenesulfinates and 8-alkyl-2-naphthalenesulfinates. Examples of the anion in which X is a phosphorus atom include dodecylbenzenephosphonates, mesitylenephosphonates, 4-t-butyl-2,6-dimethylbenzenephosphonates; toluenephosphonates, ethylbenzenephosphonates, alkyl propylbenzene phosphonates, butylbenzenephosphonates, octylbenzenephosphonates or laurylbenzenephosphonates, in which the position of the alkyl group with respect to the phosphonate group is any of the para, meta and ortho positions; alkyl 2,4-dimethylbenzenephosphonates, alkyl 2-naphthalenephosphonates, alkyl 1-alkyl-2-naphthalenephosphonates, alkyl 3-alkyl-2-naphthalenephosphonates, alkyl 4-alkyl-2-naphthalenephosphonates, alkyl 5-alkyl-2-naphthalenephosphonates, alkyl 6-alkyl-2-naphthalenephosphonates, alkyl 7-alkyl-2-naphthalenephosphonates, alkyl 8-alkyl-2-naphthalenephosphonates, bis(dodecylphenyl)phosphinate, bis(1,3,5-trimethylphenyl)phosphinate, bis(4-t-butyl-2,6-dimethylphenyl)phosphinate; bis(methylphenyl)phosphinate, bis(ethylphenyl)phosphinate, bis(propylphenyl)phosphinate, bis(butylphenyl)phosphinate, bis(octylphenyl)phosphinate or bis(laurylphenyl)phosphinate, in which the position of the alkyl group with respect to the phosphinate group is any of the para, meta and ortho positions; bis(2,4-dimethylphenyl)phosphinate, bis(2-naphthalene)phosphinate, bis(1-alkyl-2-naphthalene)phosphinates, bis(3-alkyl-2-naphthalene)phosphinates, bis(4-alkyl-2-naphthalene)phosphinates, bis(5-alkyl-2-naphthalene)phosphinates, bis(6-alkyl-2-naphthalene)phosphinates, bis(7-alkyl-2-naphthalene)phosphinates and bis(8-alkyl-2-naphthalene)phosphinates. Further, examples of the anion in which X is a carbon atom include dodecylbenzenecarboxylate, mesitylenecarboxylate, 4-t-butyl-2,6-dimethylbenzenecarboxylate; toluenecarboxylate, ethylbenzenecarboxylate, propylbenzenecarbosylate, butylbenzenecarboxylate, octylbenzenecarboxylate or laurylbenzenecarboxylate, in which the position of the alkyl group with respect to the carboxylate group is any of the para, meta and ortho positions; 2,4-dimethylbenzenecarboxylate, 2-naphthalenecarboxylate, 1-alkyl-2-naphthalenecarboxylates, 3-alkyl-2-naphthalenecarboxylates, 4-alkyl-2-naphthalenecarboxylates, 5-alkyl-2-naphthalenecarboxylates, 6-alkyl-2-naphthalenecarboxylates, 7-alkyl-2-naphthalenecarboxylates and 8-alkyl-2-naphthalenecarboxylates.

As the ionic compound (1), one in which X is a sulfur atom, particularly one in which X is a sulfur atom, and n is 1, that is, one represented by the following general formula (1A) is preferable from the viewpoint of easy availability and ease of synthesis of the ionic compound (1).

[Formula 1A]

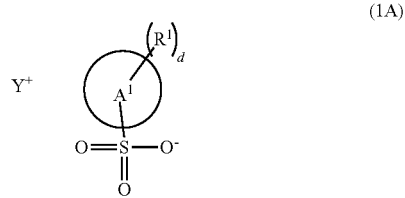

(1A)

wherein the ring $A^1$, $R^1$, d and $Y^+$ have the same meanings as in the above formula (1).

It is preferable because the advantage of the present invention is made to become better that the molecular weight of the anion in the general formula (1) be 150 or higher and 850 or lower, and especially 200 or higher and 500 or lower.

Especially preferable cations represented by $Y^+$ in the general formula (1) include a phosphonium cation, an ammonium cation, a pyridium cation, an imidazolium cation and a pyrrolidium cation. In the present invention, at least one selected from these cations is preferably used. Particularly when the cation represented by $Y^+$ in the general formula (1) is a phosphonium cation or an ammonium cation, especially a phosphonium cation, it is preferable because the compatibility with the light-emitting material becomes higher.

Examples of the phosphonium cations or the ammonium cations include cations represented by the following general formula (2).

[Formula 2]

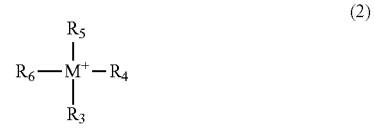

(2)

wherein $R_3$, $R_4$, $R_5$ and $R_6$ each denote an alkyl group, an alkoxyalkyl group, a trialkylsilylalkyl group, an alkenyl group, an alkynyl group, an aryl group or a heterocyclic group, which each may be substituted with a substituent; $R_3$, $R_4$, $R_5$ and $R_6$ may be identical with or different from one another; and M denotes N or P.

The alkyl groups, represented by $R_3$, $R_4$, $R_5$ and $R_6$ may be any of branched-chain, straight-chain and cyclic ones, but are preferably branched-chain or straight-chain ones. Examples of the branched-chain or straight-chain alkyl groups include the groups cited above as examples of branched-chain or straight-chain alkyl groups represented by R' of the above-mentioned general formula (1). Examples of the cyclic alkyl groups include the groups cited above as examples of cyclic alkyl groups represented by R' of the above-mentioned general formula (1).

Examples of the alkoxyalkyl groups represented by $R_3$, $R_4$, $R_5$ and $R_6$ include alkoxides of the above-mentioned branched-chain or straight-chain alkyl groups represented by R' of the above-mentioned general formula (1). Examples of the branched-chain or straight-chain alkyl groups in the alkoxyalkyl groups include the groups cited above as examples of branched-chain or straight-chain alkyl groups represented by R' of the above-mentioned general formula (1).

Examples of the alkyl groups in the trialkylsilylalkyl groups represented by $R_3$, $R_4$, $R_5$ and $R_6$ include the groups cited above as examples of branched-chain or straight-chain alkyl groups represented; by R' of the above-mentioned general formula (1).

Examples of the alkenyl groups and the alkynyl groups represented by $R_3$, $R_4$, $R_5$ and $R_6$ include the groups obtained by making one of carbon-carbon single bonds in the branched-chain or straight-chain alkyl groups represented by R' of the above-mentioned general formula (1) to be a carbon-carbon double bond or a carbon-carbon triple bond. Specific examples of the alkenyl groups include straight-chain or branched-chain alkenyl groups such as a vinyl group, an allyl group, an isopropenyl group, a 2-butenyl group, a 2-methylallyl group, a 1,1-dimethylallyl group, a 3-methyl-2-butenyl group, a 3-methyl-3-butenyl group, 4-pentenyl group, a hexenyl group, an octenyl group, a nonenyl group and a decenyl group. Examples of the alkynyl groups include an ethynyl group and a prop-2-yn-1-yl group.

Examples of the aryl groups represented by $R_3$, $R_4$, $R_5$ and $R_6$ include a phenyl group, a tolyl group, a xylyl group, a naphthyl group, and an anthracenyl group, a methylphenyl group and a dimethylphenyl group. Further, examples of the heterocyclic groups represented by $R_3$, $R_4$, $R_5$ and $R_6$ include monovalent groups derived from, for example, pyridine, pyrrole, furan, imidazole, pyrazole, oxazole, imidazoline and pyrazine.

In each group cited above as groups represented by $R_3$, $R_4$, $R_5$ and $R_6$, one or two or more hydrogen atoms out of hydrogen atoms contained therein may be replaced with a substituent. Examples of the substituents include halogen atoms, an amino group, a nitrile group, a phenyl group, a benzyl group, a carboxyl group and alkoxy groups having 1 or more and 12 or less carbon atoms.

In each group cited above as the groups represented by $R_3$, $R_4$, $R_5$ and $R_6$, a part of hydrogen atoms contained therein may be replaced with fluorine atom(s). Introduction of fluorine atoms, since improving the voltage withstandability, leads to the stability and the elongated life of the light-emitting electrochemical cell.

In the ionic compound in which the cation is a phosphonium cation or an ammonium cation, from the viewpoint of the compatibility with the light-emitting material and the voltage withstandability, it is preferable that one or two or more groups among the above $R_3$, $R_4$, $R_5$ and $R_6$ be alkyl groups, and it is more preferable that any group thereof be an alkyl group. Then, from the viewpoint of more enhancing the voltage withstandability and more improving the compatibility with the light-emitting material, the number of carbon atoms of the alkyl groups represented by $R_3$, $R_4$, $R_5$ and $R_6$ is preferably 1 or larger and 24 or smaller, more preferably 2 or larger and 20 or smaller, still more preferably 4 or larger and 18 or smaller, and further still more preferably 4 or larger and 16 or smaller.

It is especially preferable that 2, 3 or 4 groups among $R_3$, $R_4$, $R_5$ and $R_6$ be alkyl groups having the same number of carbon atoms. Particularly when 2, 3 or 4 groups among $R_3$, $R_4$, $R_5$ and $R_6$ are alkyl groups having the same number of carbon atoms, from the similar viewpoint as in the above, the number of carbon atoms of the alkyl groups having the same number of carbon atoms is preferably 1 or larger and 12 or smaller, more preferably 2 or larger and 10 or smaller, and especially preferably 4 or larger and 8 or smaller.

It is preferable that the molecular weight of the phosphonium cation or the ammonium cation in the general formula (2) be 70 or higher and 800 or lower, and especially 120 or higher and 600 or lower because the advantage of the present invention becomes better.

Examples of the phosphonium ions include a tetraethylphosphonium ion, a triethylmethylphosphonium ion, a triethylpentylphosphonium ion, a tetrapropylphosphonium ion, a tripropylmethylphosphonium ion, tripropylethylphosphonium ion, a tetra(n-butyl)phosphonium ion, a tri(n-butyl)methylphosphonium ion, a tri(n-butyl)ethylphosphonium ion, a tri(n-butyl)octylphosphonium ion, a tri(n-butyl)dodecylphosphonium ion, a tetra(n-hexyl)phosphonium ion, a tri(n-hexyl)methylphosphonium ion, an ethyltri(n-hexyl) phosphonium ion, a butyltri(n-hexyl) phosphonium ion, a tetradecyltri(n-hexyl)phosphonium ion, a tri(n-octyl)(n-hexadecyl)phosphonium ion, a tri(n-octyl)(n-dodecyl)phosphonium ion, a tetra(n-octyl)phosphonium ion, a tri(n-octyl)(n-butyl)phosphonium ion, a tri(n-octyl)ethylphosphonium ion and a tri(n-octyl)methylphosphonium ion. Then, examples of the ammonium ions include a tetraethylammonium ion, a triethylmethyiammonium ion, a tetrapropylammonium ion, a tripropylmethylammonium ion, a tripropylethylammonium ion, a tetra(n-butyl)ammonium ion, a tri(n-butyl)methylammonium ion, a tri(n-butyl)ethylammonium ion, a tetra(n-hexyl)ammonium ion, a tri(n-hexyl)methylammonium ion, an ethyltri(n-hexyl)ammonium ion, a butyltri(n-hexyl)ammonium ion, a tri(n-octyl)(n-butyl)ammonium ion, a tri(n-octyl)ethylammonium ion and a tri(n-octyl) methylammonium ion.

In the general formula (2), hydrogen atoms bonded to carbon constituting the above-mentioned saturated aliphatic groups represented by $R_3$, $R_4$, $R_5$ and $R_6$ may partially be replaced with a fluorine atom. The introduction of the fluorine atom, since improving the voltage withstandability, leads to the stability and the life elongation of the light-emitting electrochemical cell.

The ionic compound (1) may be solid or liquid at normal temperature (25° C.), The ionic compound (1) makes a solid state or a liquid state depending on the combination of a cation and an anion to be selected and the structure of the cation. In the present invention, the ionic compound (1) can be used singly or in a combination of two or more thereof. When a plurality of ionic compounds (1) are used, all of these may be solid at normal temperature or all of these may be liquid at normal temperature. Further, at least one thereof may be liquid at normal temperature and simultaneously, at least one thereof may be solid at normal temperature.

The ionic compound (1), when the cation is a phosphonium ion, can be obtained, for example, by using a quaternary phosphonium halide obtained by reacting a tertiary phosphine compound corresponding to the phosphonium cation concerned with a halogenated hydrocarbon compound, and reacting and anion-interchanging the quaternary phosphonium halide with a metal salt having the anion component. Also if the cation is an ammonium ion, an ion liquid can be obtained similarly by using a quaternary ammonium halide obtained by reacting a tertiary amine compound, with a halogenated hydrocarbon compound.

As described above, as the light-emitting material, contained in the light-emitting layer 12, an organic polymeric light-emitting material may be used or a combination of one or two or more luminous substances selected from metal complexes, organic low-molecular materials and quantum dot materials with an organic polymeric conductive material (including both a luminous conductive material and a non-luminous conductive material) may be used.

Here, the compound represented by the general formula (1) can be used also as an ionic compound for the light-emitting layer of the light-emitting electrochemical cell. Further, the compound represented by the general formula (1) can be used also as one component of an ionic composition (or ion liquid) for the light-emitting layer of the light-emitting electrochemical cell. Such an ionic compound and an ionic composition for the light-emitting layer are used to be added in the light-emitting layer of the light-emitting electrochemical cell, and usually added in the light-emitting layer by being combined with the light-emitting material. Other points of the ionic compound for the light-emitting layer are as described in detail in above-mentioned and later-mentioned descriptions of the light-emitting electrochemical cell.

In the light-emitting electrochemical cell of the present embodiment, the content proportion of the ionic compound (1) in the light-emitting layer 12 is preferably 1% by mass or higher and 30% by mass or lower, and more preferably 5% by mass or higher and 20% by mass or lower from the viewpoint of securing the ion mobility and enhancing the film formability of the light-emitting layer 12. The content of the ionic compound (1) in the light-emitting layer 12 is preferably 10 part by mass or higher and 25 parts by mass or lower to 100 parts by mass of the light-emitting material. The amount mentioned herein of the light-emitting material is, in the case of using an organic polymeric light-emitting material as the light-emitting material, an amount of the organic polymeric light-emitting material, and in the case of using, as the light-emitting material, a combination of a luminous substance such as a metal complex, an organic low-molecular material or a quantum dot material with an organic polymeric conductive material, a total amount of the luminous substance such as the metal complex, the organic low-molecular material or the quantum dot material, and the organic polymeric conductive material. Here, In the light-emitting electrochemical cell of the present invention, there can also be used, in addition to the ionic compound (1), an ionic compound (for example, ion liquid) other than the ionic compound (1); and the content of the ionic compound other than the ionic compound (1) in this case is, with respect to 100 parts by mass of the ionic compound (1), preferably 100 parts by mass or lower, and more preferably 50 parts by mass or lower.

The organic polymeric light-emitting materials include various types of π-conjugated polymers. Specific examples thereof include para-phenylene vinylene, fluorene, 1,4-phenylene, thiophene, pyrrole, para-phenylene sulfide, benzothiazole, biothiophene, and polymers of derivatives in which substituents are incorporated in these, and copolymers containing these. Such substituents include alkyl groups having 1 or more and 20 or less carbon atoms, alkoxy groups having 1 or more and 20 or less carbon atoms, aryl groups having 6 or more and 18 or less carbon atoms, and groups represented by $[(-CH_2CH_2O-)_nCH_3]$ (n is an integer of 1 or more and 10 or less). Further the copolymers include those made by bonding repeating units of two or more polymers among the above-cited n-conjugated polymers. The arrangement of the each repeating unit in the copolymer includes random arrangement, alternating arrangement, block arrangement and combinations thereof. There are especially preferably used fluorene, para-phenylene vinylene, polymers of derivatives in which substituents are incorporated in these, and copolymers containing these. Further as the organic polymeric light-emitting material, commercially available products can also be used. Examples of such commercially available products include a compound available from Solaris Chem Inc., under the name of SOL2412, Poly[(9,9-dioctylfluorenyl-2,7-diyl)-alt-co-(9,9'-spirobifluorene-2,7-diyl)], a compound available from Merck KGaA., under the name of PBY-132, phenylene-substituted poly(para-phenylene vinylene), and a compound available from Sigma-Aldrich Corp., poly[(9,9-di-n-octylfluorenyl-2,7-diyl)-alt-(benzo[2,1,3]thiadiazol-4,8-diyl)]. These can be used singly or in a combination of two or more.

As the metal complex, there can be used well-known ones conventionally used as light-emitting materials in organic EL, and examples thereof include phosphorescent emitters such as a tris(8-quinolinolate) aluminum complex, a tris(4-methyl-8-quinolinolate) aluminum complex, a bis(8-quinolinolate) zinc complex, a tris(4-methyl-5-trifluoromethyl-8-quinolinolate) aluminum complex, a tris(4-methyl-5-cyano-8-quinolinolate) aluminum complex, a bis(2-methyl-5-trifluoromethyl-8-quinolinolate)[4-(4-cyanophenyl) phenolate] aluminum complex, a bis(2-methyl-5-cyano-8-quinolinolate)[4-(4-cyanophenyl)phenolate] aluminum complex, a tris(8-quinolinolate) scandium complex, and a bis[8-(para-tosyl)aminoquinoline] zinc complex, cadmium complex and Ir complex, ruthenium complexes having bipyridyl (bpy) or derivatives thereof, or phenanthroline or derivatives thereof, and a platinum octaethylporphyrin complex as their ligands. These can be used singly or in a combination of two or more.

As the organic low-molecular material, there can be used well-known ones conventionally used as light-emitting materials in organic EL, and examples thereof include fluorescent emitters such as 9,10-diarylanthracene derivatives, pyrene, coronene, perylene, rubrene, 1,1,4,4-tetraphenylbutadiene, 1,2,3,4-tetraphenylcyclopentadiene, pentaphenylcyclopentadiene, poly-2,5-diheptyloxy-para-phenylene vinylene, coumalin-based fluorescent substances, perylene-based fluorescent substances, pyran-based fluorescent substances, anthrone-based fluorescent substances, porphyrin-based fluorescent substances, quinacridone-based fluorescent substances, N,N'-dialkyl-substituted quinacridone-based fluorescent substances, naphthalimide-based fluorescent substances, and N,N'-diaryl-substituted pyrrolo-pyrrole-based fluorescent substances. These can be used singly or in a combination of two or more. Here, the organic low-molecular material mentioned herein means not being an organic compound obtained by some polymerization reaction.

When the light-emitting material contained in the light-emitting layer 12 is a quantum dot material, as the quantum dot material, there can be used a single substance of C, Si, Ge, Sn, P, Se, Te or the like, besides, a combination, of Zn, Cd, Hg, Pb or the like, which becomes a divalent cation, with O, S, Se, Te or the like, which becomes a divalent anion, a combination of Ga, In or the like, which becomes a trivalent cation, with N, P, As, Sb or the like, which becomes a trivalent anion, or a composite combination thereof. Specific examples of these combinations include GaN, GaP, CdS, CdSe, CdTe, InP, InN, ZnS, $In_2S_3$, ZnO, CdO, composites thereof and mixtures thereof. As the composite combination, chalcopyrite-type compounds can also be used, and examples thereof include $CuAlS_2$, $CuGaS^2$, $CuInS^2$, $CuAlSe^2$, $CuGaSe^2$, $AgAlS^2$, $AgGaS^2$, $AgInS^2$, $AgAlSe^2$, $AgGaSe^2$, $AgInSe^2$, $AgAlTe^2$, $AgGaTe^2$, $AgInTe^2$, $Cu(In,Al)Se^2$, $Cu(In,Ga)(S,Se)^2$, $Ag(In,Ga)Se_2$ and $Ag(In,Ga)(S,Se)_2$. These can be used singly or in a combination of two or more.

The organic polymeric conductive materials to transport electrons and/or holes include polyvinylcarbazole, polyphenylene, polyfluorene, polyaniline, polythiophene, polypyrrole, polyphenylene vinylene, poiythienylene vinylene, polyquinoline, and polyquinoxaline. Further the organic polymeric light-emitting materials described above can also be used as organic polymeric conductive materials because having the transporting functions of electrons and/or holes. These can be used singly or in a combination of two or more.

In these light-emitting materials, from the viewpoint of making their function to be sufficiently exhibited, the content proportion thereof in the light-emitting layer 12 is, in the case of using an organic polymeric light-emitting material, preferably 60% by mass or higher and 99% by mass or lower, and more preferably 70% by mass or higher and 98% by mass or lower. Further in the case of using a combination of a luminous substance such as a metal complex, an organic low-molecular material or a quantum dot material with an organic polymeric conductive material, the proportion of the total amount thereof in the light-emitting layer 12 is preferably 60% by mass or higher and 99% by mass or lower, and more preferably 70% by mass or higher and 98% by mass or lower.

Further in the case of using a combination of a luminous substance such as a metal complex, an organic low-molecular material or a quantum dot material with an organic polymeric conductive material, the proportion of the organic polymeric conductive material to 100 parts by mass of the luminous substance such as the metal complex, the organic low-molecular material or the quantum dot material is preferably 5 parts by mass or higher and 25 parts by mass or lower.

The light-emitting layer 12 may comprise substances other than the light-emitting material and the ionic compound. Examples of such substances include surfactants, and polymer components (polystyrene, polymethyl methacrylate (PMMA) and the like) to improve the film formability. Further in the case of using an organic polymeric light-emitting material as the light-emitting material, organic polymeric conductive materials such as polyvinylcarbazole are also included in the other components. The amount of the components (excluding solvent) other than the light-emitting material and the ionic compound (1) in the light-emitting layer 12 is made to be, with respect to 100 parts by mass of the whole light-emitting layer 12, preferably 30 parts by mass or smaller, still more preferably 20 parts by mass or smaller, and especially preferably 10 parts by mass or smaller.

The film thickness of the light-emitting layer 12 thus constituted is preferably 20 nm or larger and 300 nm or smaller, and more preferably 50 nm or larger and 150 nm or smaller. When the film thickness of the light-emitting layer 12 is in this range, it is preferable from the viewpoint that light emission can be provided sufficiently and efficiently by the light-emitting layer 12, and defects in a predetermined light-emitting portion can be suppressed, to thereby prevent short circuit.

A light-emitting electrochemical cell 10 of the present embodiment can be produced, for example, by the following production method. First, a substrate installed with a first electrode 13 is prepared. When the first electrode 13 is formed, for example, of an ITO, the first electrode 13 composed of the ITO on the surface of the substrate can be formed by forming a vapor-deposited film of the ITO in a patterned shape by using a photolithography process or a combination of a photolithography process and a lift-off process on the surface of the glass substrate and the like.

Then, an ionic compound (1) and a light-emitting material are dissolved in a solvent to thereby prepare a composition for forming a light-emitting layer of the light-emitting electrochemical cell. From the viewpoint of efficiently mixing the ionic compound (1) and the light-emitting material, the solvent is usually an organic solvent, and specifically, it is preferable that the solvent contain at least one organic solvent selected from the group consisting of toluene, benzene, tetrahydrofuran, carbon disulfide, dimethyl chloride, chlorobenzene and chloroform. In this case, the organic solvent can be used only singly or only as a combination of two or more thereof. Alternatively, other organic solvents such as methanol and ethanol may also be used by being mixed therewith, in the range not impairing properties such as solubility of these compounds. That is, the organic solvent dissolving the ionic compound (1) and the light-emitting material can contain at least one organic solvent selected from the group consisting of toluene, benzene, tetrahydrofuran, carbon disulfide, dimethyl chloride, chlorobenzene and chloroform, and organic solvents other than the at least one organic solvent.

With respect to the blend ratio (mass ratio) of the ionic compound and the light-emitting material in the composition for forming a light-emitting layer, the former:the latter is preferably 1:4 to 100. The amount of the solvent is preferably an amount dissolving the light-emitting material and the ionic compound each in a concentration of 2 g/L or higher and 20 g/L or lower. The amount of the light-emitting material mentioned herein is, in the case of using an organic polymeric light-emitting material as the light-emitting material, an amount of the organic polymeric light-emitting material, and in the case of using, as the light-emitting material, a combination of a luminous substance such as a metal complex, an organic low-molecular material or a quantum dot material with an organic polymeric conductive material, a total amount of the luminous substance such as the metal complex, the organic low-molecular material or the quantum dot material and the organic polymeric conductive material. The composition for forming a light-emitting layer is applied on the first electrode 13 of the substrate by a spin coating method or the like. Thereafter, a coating film formed by this application is dried to evaporate the organic solvent to thereby form a light-emitting layer 12. The preparation of the composition for forming a light-emitting layer and the formation of the light-emitting layer 12 are preferably carried out in an inert gas atmosphere having preferably a moisture rate of 100 ppm or less. The inert gas in this case includes argon, nitrogen and helium. Then, since mingling of foreign matter such as suspended particles in the light-emitting layer causes formation of non-light-emitting portions, it is preferable that the preparation of the composition for forming the light-emitting layer and the formation of the light-emitting layer 12 be carried out in a clean room or a glove box. The cleanliness is preferably Class 10000 or less, and especially preferably Class 1000 or less. Other points of the composition for forming the light-emitting layer are as described in detail in above-mentioned and later-mentioned descriptions of the light-emitting electrochemical cell.

Then, a second electrode 14 is formed on the formed light-emitting layer 12. In this case, a predetermined patterned electrode is formed on the light-emitting layer 12, for example, by vapor-depositing aluminum (Al) into a film form by a vacuum vapor-deposition process through a mask. The second electrode 14 is thus formed on the light-emitting layer 12. Thereby, a light-emitting electrochemical cell 10 illustrated in FIG. 1 is obtained.

The light-emitting electrochemical cell 10 of the present embodiment emits light by the following emission mechanism. As illustrated in FIGS. 2(a) and 2(b), a voltage is applied to the light-emitting layer 12 so that the first electrode 13 becomes an anode and the second electrode 14 becomes a cathode. Thereby, ions in the light-emitting layer 12 migrate along an electric field and a layer where anion species gather is formed in the vicinity of the interface with the first electrode 13 in the light-emitting layer 12. On the other hand, a layer where cation species gather is formed in the vicinity of the interface with the second electrode 14 in the light-emitting layer 12. Electric double layers are thus formed on the respective electrodes. Thereby, holes are doped from the first electrode 13 being an anode into the light-emitting layer 12 to thereby spontaneously form a p-doped region 16 in the vicinity of the first electrode 13; and electrons are doped from the second electrode 14 being a cathode into the light-emitting layer 12 to thereby spontaneously form an n-doped region 17 in the vicinity of the second electrode 14. Then, these doped regions constitute a high-carrier density p-i-n junction. Thereafter, holes and electrons are injected from the p-doped region 16 and the n-doped region 17, respectively, and excitons are formed and recombine in the i-layer. The light-emitting layer 12 is excited by the energy of the excitons. The excited light-emitting layer 12 returns to a ground state to thereby emit light. Light, emission from the light-emitting layer 12 can thus be provided. In order to obtain light, of a desired wavelength, it suffices if there is selected a light-emitting material having an energy difference (band gap) between the highest occupied molecular orbital and the lowest unoccupied molecular orbital corresponding to the desired wavelength.

In the ionic compound for the light-emitting layer and the composition for forming the light-emitting layer of the light-emitting electrochemical cell and the light-emitting electrochemical cell, using the compound represented by the general formula (1), the use of the ionic compound represented by the general formula (1) together with a light-emitting material for emission layer formation provides a higher luminance at a low voltage than use of other ionic compounds, and stabilizes the voltage required for providing a certain luminance. Such a light-emitting electrochemical cell is high in the luminous efficiency and high in the reliability. Further, the light-emitting electrochemical cell of the present invention, which uses the ionic compound (1) high in the electrochemical stability and capable of improving the luminous efficiency, even when a high voltage is applied, can stably provide light emission of a high luminance.

EXAMPLES

Hereinafter, the present invention will be described in detail by way of Examples, but the present invention is not limited thereto. A property in the following Examples was measured by the following method.
Emission Luminance
A first electrode of a light-emitting electrochemical cell is connected to a positive pole of a direct current, and a second electrode thereof is connected to a negative pole thereof; a voltage is applied at a sweeping rate of 1 V/sec up to 15 V, and the maximum value in the luminance during the application was measured as an emission luminance. The measurement was carried out by using a CS-2000 (manufactured by Konica Minolta, Inc.).
Voltage Withstandability
A first electrode of a light-emitting electrochemical cell was connected to a positive pole of a direct current, and a second electrode thereof is connected to a negative pole thereof; and a current of 100 µA was made to flow for 72 hours, during which the over-time change in the voltage was measured. The measurement was carried out by a 2400 SourceMeter (manufactured by Keithley Instruments Inc.).

Example 1 and Comparative Example 1

A commercially available glass substrate with an ITO film (manufactured by Geomatec Co., Ltd., ITO film thickness: 200 nm) was used as a first electrode 13.

PFO-spiro (poly[(9,9-dioctylfluorenyl-2,7-diyl)-alt-co-(9, 9'-spirobifluorene-2,7-diyl)], manufactured by Solaris Chem Inc., model number: SOL2412) as an organic polymeric light-emitting material, and an ionic compound indicated in Table 1 were mixed to thereby prepare respective mixed solutions. Specifically, in a glove box in an argon atmosphere at room temperature, a toluene solution (concentration: 9 g/L) of the organic polymeric light-emitting material, and a toluene solution (concentration: 9 g/L) of the ionic compound were mixed in a volume ratio of the solution of the organic polymeric light-emitting material:the solution of the ionic compound=4:1 to thereby prepare respective compositions for forming light-emitting layers.

Then, in a glove box in an argon atmosphere at room temperature, the prepared composition, for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed.

Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in the following Table 1.

TABLE 1

| | Ionic Compound | | Emission Luminance | Organic Polymeric Light-Emitting | Emission |
| --- | --- | --- | --- | --- | --- |
| | Cation | Anion | (cd/m$^2$) | Material | Color |
| Example 1-1 | tetrabutylphosphonium $P(C_4H_9\text{-}n)_4^+$ | mesitylenesulfonate $2,4,6\text{-}(CH_3)_3(C_6H_2)SO_3^-$ | 12,500 | PFO-spiro[1] | blue |
| Example 1-2 | tetrabutylphosphonium $P(C_4H_9\text{-}n)_4^+$ | dodecylbenzenesulfonate (hard type) $(C_{12}H_{25})(C_6H_4)SO_3^-$ | 1,040 | | |
| Example 1-3 | tributyloctylphosphonium $P(C_4H_9\text{-}n)_3(C_8H_{17}\text{-}n)^+$ | dodecylbenzenesulfonate (hard type) $(C_{12}H_{25})(C_6H_4)SO_3^-$ | 1,600 | | |
| Example 1-4 | tributyldodecylphosphonium $P(C_4H_9\text{-}n)_3(C_{12}H_{25}\text{-}n)^+$ | dodecylbenzenesulfonate (hard type) $(C_{12}H_{25})(C_6H_4)SO_3^-$ | 970 | | |
| Example 1-5 | tetraoctylphosphonium $P(C_8H_{17}\text{-}n)_4^+$ | p-toluenesulfonate $p\text{-}(CH_3)(C_6H_4)SO_3^-$ | 1,690 | | |
| Example 1-6 | tetraoctylphosphonium $P(C_8H_{17}\text{-}n)_4^+$ | dodecylbenzenesulfonate (hard type) $(C_{12}H_{25})(C_6H_4)SO_3^-$ | 820 | | |

TABLE 1-continued

| | Ionic Compound | | Emission Luminance | Organic Polymeric Light-Emitting | Emission |
|---|---|---|---|---|---|
| | Cation | Anion | (cd/m$^2$) | Material | Color |
| Example 1-7 | trioctyldodecylphosphonium P(C$_8$H$_{17}$-n)$_3$(C$_{12}$H$_{25}$-n)$^+$ | dodecylbenzenesulfonate (hard type) (C$_{12}$H$_{25}$)(C$_6$H$_4$)SO$_3^-$ | 1,160 | | |
| Example 1-8 | trioctylhexadecylphosphonium P(C$_8$H$_{17}$-n)$_3$(C$_{16}$H$_{33}$-n)$^+$ | p-toluenesulfonate p-(CH$_3$)(C$_6$H$_4$)SO$_3^-$ | 1,320 | | |
| Example 1-9 | trioctylhexadecylphosphonium P(C$_8$H$_{17}$-n)$_3$(C$_{16}$H$_{33}$-n)$^+$ | mesitylenesulfonate 2,4,6-(CH$_3$)$_3$(C$_6$H$_2$)SO$_3^-$ | 2,090 | | |
| Example 1-10 | trioctylhexadecylphosphonium P(C$_8$H$_{17}$-n)$_3$(C$_{16}$H$_{33}$-n)$^+$ | 2,4-dimethylbenzenesulfonate 2,4-(CH$_3$)$_2$(C$_6$H$_3$)SO$_3^-$ | 1,330 | | |
| Comparative Example 1-1 | tributyldodecylphosphonium P(C$_4$H$_9$-n)$_3$(C$_{12}$H$_{25}$-n)$^+$ | acetate CH$_3$COO$^-$ | 220 | | |
| Comparative Example 1-2 | tetraoctylphosphonium P(C$_8$H$_{17}$-n)$_4^+$ | acetate CH$_3$COO$^-$ | 100 | | |
| Comparative Example 1-3 | trioctyldodecylphosphonium P(C$_8$H$_{17}$-n)$_3$(C$_{12}$H$_{25}$-n)$^+$ | acetate CH$_3$COO$^-$ | 200 | | |

[1] PFO-spiro . . . Poly[(9,9-dioctylfluorenyl-2,7-diyl)-alt-co-(9,9'-spirobifluorene-2,7-diyl)], manufactured by Solaris Chem Inc., model number: SOL2412

It is clear from the results indicated in Table 1 that in the sweeping up to 15 V, the light-emitting electrochemical cells in Examples 1-1 to 1-10 using ionic compounds represented by the general formula (1) provided a higher-luminance light emission and were better in the luminous efficiency than Comparative Examples 1-1 to 1-3 using the ionic compounds not corresponding to the general formula (1).

Examples 2 and Comparative Examples 2

A commercially available glass substrate with an ITO film (manufactured by Geomatec Co., Ltd., ITO film thickness: 200 nm) was used as a first electrode 13.

Super Yellow (phenylene-substituted poly(para-phenylene vinylene), manufactured by Merck KGaA, product name: PDY-132) as an organic polymeric light-emitting material, and an ionic compound indicated in Table 1 were mixed to thereby prepare respective mixed solutions. After this operation, the same processes as in Examples 1 were carried out. The results of measurements of the luminous property of the obtained light-emitting electrochemical cells 10 are shown in the following Table 2. Further in Examples 2-4, 2-7 and 2-8 and Comparative Examples 2-2, 2-4 and 2-6, in order to evaluate the voltage withstandability, the over-time change in the voltage was measured. The results are shown in FIGS. 3 to 8.

TABLE 2

| | Ionic Compound | | Emission Luminance | Organic Polymeric Light-Emitting | Emission |
|---|---|---|---|---|---|
| | Cation | Anion | (cd/m$^2$) | Material | Color |
| Example 2-1 | tetrabutylphosphonium P(C$_4$H$_9$-n)$_4^+$ | dodecylbenzenesulfonate (hard type) (C$_{12}$H$_{25}$)(C$_6$H$_4$)SO$_3^-$ | 4,200 | Super Yellow[2] | yellow |
| Example 2-2 | tributyloctylphosphonium P(C$_4$H$_9$-n)$_3$(C$_8$H$_{17}$-n)$^+$ | dodecylbenzenesulfonate (hard type) (C$_{12}$H$_{25}$)(C$_6$H$_4$)SO$_3^-$ | 5,990 | | |
| Example 2-3 | tributyldodecylphosphonium P(C$_4$H$_9$-n)$_3$(C$_{12}$H$_{25}$-n)$^+$ | dodecylbenzenesulfonate (hard type) (C$_{12}$H$_{25}$)(C$_6$H$_4$)SO$_3^-$ | 6,200 | | |
| Example 2-4 | trioctyldodecylphosphonium P(C$_8$H$_{17}$-n)$_3$(C$_{12}$H$_{25}$-n)$^+$ | dodecylbenzenesulfonate (hard type) (C$_{12}$H$_{25}$)(C$_6$H$_4$)SO$_3^-$ | 6,300 | | |
| Example 2-5 | trioctylhexadecylphosphonium P(C$_8$H$_{17}$-n)$_3$(C$_{16}$H$_{33}$-n)$^+$ | p-(n-octyl)benzenesulfonate p-(C$_8$H$_{17}$-n)(C$_6$H$_4$)SO$_3^-$ | 7,350 | | |
| Example 2-6 | trioctylhexadecylphosphonium P(C$_8$H$_{17}$-n)$_3$(C$_{16}$H$_{33}$-n)$^+$ | p-toluenesulfonate p-(CH$_3$)(C$_6$H$_4$)SO$_3^-$ | 6,930 | | |
| Example 2-7 | trioctylhexadecylphosphonium P(C$_8$H$_{17}$-n)$_3$(C$_{16}$H$_{33}$-n)$^+$ | mesitylenesulfonate 2,4,6-(CH$_3$)$_3$(C$_6$H$_2$)SO$_3^-$ | 7,000 | | |
| Example 2-8 | trioctylhexadecylphosphonium P(C$_8$H$_{17}$-n)$_3$(C$_{16}$H$_{33}$-n)$^+$ | 2,4-dimethylbenzenesulfonate 2,4-(CH$_3$)$_2$(C$_6$H$_3$)SO$_3^-$ | 7,020 | | |
| Comparative Example 2-1 | tributyldodecylphosphonium P(C$_4$H$_9$-n)$_3$(C$_{12}$H$_{25}$-n)$^+$ | acetate CH$_3$COO$^-$ | 2,518 | | |
| Comparative Example 2-2 | tetrabutylphosphonium P(C$_4$H$_9$-n)$_4^+$ | n-butanesulfonate (C$_4$H$_9$-n)SO$_3^-$ | 15 | | |
| Comparative Example 2-3 | tributyldodecylphosphonium P(C$_4$H$_9$-n)$_3$(C$_{12}$H$_{25}$-n)$^+$ | benzenesulfonate (C$_6$H$_5$)SO$_3^-$ | 9 | | |
| Comparative Example 2-4 | tetraoctylphosphonium P(C$_8$H$_{17}$-n)$_4^+$ | acetate CH$_3$COO$^-$ | 2,454 | | |

TABLE 2-continued

| | Ionic Compound | | Emission Luminance | Organic Polymeric Light-Emitting | Emission |
| --- | --- | --- | --- | --- | --- |
| | Cation | Anion | (cd/m$^2$) | Material | Color |
| Comparative Example 2-5 | trioctyldodecylphosphonium P(C$_8$H$_{17}$-n)$_3$(C$_{12}$H$_{25}$-n)$^+$ | acetate CH$_3$COO$^-$ | 2,230 | | |
| Comparative Example 2-6 | tetrabutylphosphonium P(C$_4$H$_9$-n)$_4^+$ | benzoate (C$_6$H$_5$)CO$_2^-$ | 480 | | |

[2] Super Yellow . . . Phenylene-substituted poly(para-phenylene vinylene), manufactured by Merck KGaA, product name: PDY-132

It is clear from the results indicated in Table 2 that also when the kind of the light-emitting material was changed, similarly to Examples 1, the light-emitting electrochemical cells in Examples 2-1 to 2-8 provided a higher-luminance light emission and were better in the luminous efficiency than Comparative Examples 2-1 to 2-6 using the ionic compounds not corresponding to the general formula (1). Further, it is clear from the results indicated FIGS. 3 to 8 that the light-emitting electrochemical cells of Examples 2-4, 2-7 and 2-8 exhibited a smaller over-time change in the voltage and were better in the voltage withstandability and higher in the reliability than Comparative Examples 2-2, 2-4 and 2-6.

INDUSTRIAL APPLICABILITY

According to the present invention, there can be provided a light-emitting electrochemical cell high in the luminous efficiency and excellent in the stability of the voltage in order to provide a certain luminance, and a composition forming a light-emitting layer and an ionic compound for the light-emitting layer, being capable of providing the light-emitting electrochemical cell.

The invention claimed is:
1. A light-emitting electrochemical cell, having: a light-emitting layer; and an electrode disposed on each surface of the light-emitting layer,
wherein the light-emitting layer comprises a light-emitting material and an ionic compound; and
the ionic compound is represented by the following general formula (1):

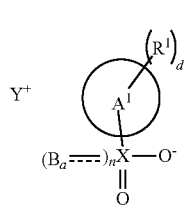

(1)

wherein the ring A$^1$ denotes an aromatic ring;
X denotes a sulfur atom, a carbon atom or a phosphorus atom;
R$^1$ denotes R' or OR', and R' denotes an alkyl group;
n denotes 0 or 1;
B denotes an oxygen atom, OR' or A$^2$, R$^2$ denotes a saturated hydrocarbon group, and A$^2$ denotes an aromatic ring which may be identical with or different from the ring A$^1$ in the formula;
the bond a is a single bond or a double bond;
when X is a carbon atom, n is 0;

when X is a sulfur atom, n is 0 or 1, and when n is 1, the bond a between B and X is a double bond and B is an oxygen atom;
when X is a phosphorus atom, n is 1, and in this case, the bond a between B and X is a single bond and B is OR$^2$ or A$^2$;
d is 1 or more and is the number of substitutable positions in the ring A', and when d is 2 or more, a plurality of R$^1$ present may be identical or different; and
Y$^+$ denotes a phosphonium cation.
2. The light-emitting electrochemical cell according to claim 1, wherein the number of carbon atoms of the alkyl group represented by R' is 1 or larger and 12 or smaller; and d is 1 or more and 9 or less.
3. The light-emitting electrochemical cell according to claim 1, wherein X is a sulfur atom; and n is 1.
4. The light-emitting electrochemical cell according to claim 1, wherein the light-emitting material is an organic polymeric light-emitting material being a polymer of para-phenylene vinylene, fluorene, 1,4-phenylene, thiophene, pyrrole, para-phenylene sulfide, benzothiazole, biothiophene or a derivative thereof, or a copolymer containing these.
5. The light-emitting electrochemical cell according to claim 1, wherein the light-emitting material comprises, as a luminous substance, at least one or two or more selected from metal complexes, organic low-molecular materials and quantum dot materials.
6. A light-emitting electrochemical cell, using, as a material for forming a light-emitting layer, a composition comprising an ionic compound represented by the following general formula (1), a light-emitting material and a solvent:

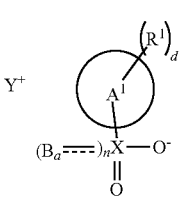

(1)

wherein the ring A$^1$ denotes an aromatic ring;
X denotes a sulfur atom, a carbon atom or a phosphorus atom;
R$^1$ denotes R' or OR', and R' denotes an alkyl group;
n denotes 0 or 1;
B denotes an oxygen atom, OR$^2$ or A$^2$, R$^2$ denotes a saturated hydrocarbon group, and A$^2$ denotes an aromatic ring which may be identical with or different from the ring A1 in the formula;
the bond a is a single bond or a double bond;

when X is a carbon atom, n is 0;
when X is a sulfur atom, n is 0 or 1, and when n is 1, the bond a between B and X is a double bond and B is an oxygen atom;
when X is a phosphorus atom, n is 1, and in this case, the bond a between B and X is a single bond and B is $OR^2$ or $A^2$;
d is 1 or more and is the number of substitutable positions in the ring $A^1$, and when d is 2 or more, a plurality of $R^1$ present may be identical or different; and
$Y^+$ denotes a phosphonium cation.

* * * * *